US012714844B2

(12) United States Patent
Tappehorn et al.

(10) Patent No.: US 12,714,844 B2
(45) Date of Patent: Aug. 25, 2026

(54) CLAMP, ESPECIALLY FOR A CONNECTION BETWEEN A VENTILATOR AND A PATIENT

(71) Applicant: Drägerwerk AG & Co. KGaA, Lübeck (DE)

(72) Inventors: Ludger Tappehorn, Lübeck (DE); Marco Monnig, Lübeck (DE); Hendrik Fischer, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 812 days.

(21) Appl. No.: 18/156,478

(22) Filed: Jan. 19, 2023

(65) Prior Publication Data

US 2023/0233832 A1 Jul. 27, 2023

(30) Foreign Application Priority Data

Jan. 24, 2022 (DE) ..................... 10 2022 101 528.9

(51) Int. Cl.
*A61M 39/28* (2006.01)
*A61M 16/08* (2006.01)
(Continued)

(52) U.S. Cl.
CPC ...... *A61M 39/284* (2013.01); *A61M 16/0816* (2013.01); *A61M 16/20* (2013.01); *F16K 7/063* (2013.01)

(58) Field of Classification Search
CPC .. A61M 39/28; A61M 39/283; A61M 39/284; A61M 39/286; A61M 16/00; A61M 16/0057; A61M 16/01; A61M 16/0497; A61M 16/0816; A61M 16/20; A61M 16/201; A61M 5/16813; F16K 7/06; F16K 7/061; F16K 7/063
See application file for complete search history.

(56) References Cited

U.S. PATENT DOCUMENTS 4,707,906 A 11/1987 Posey
6,301,756 B1 10/2001 Howard
(Continued)

FOREIGN PATENT DOCUMENTS

DE 102020000335 A1 7/2021
EP 2758698 B1 3/2017
(Continued)

*Primary Examiner* — Joseph D. Boecker
(74) *Attorney, Agent, or Firm* — McGlew and Tuttle, P.C.

(57) ABSTRACT

A clamp (1) releases or blocks a fluid connection as desired. A clamping tube (3, 4, 5.1, 5.2, 7.1) of the clamp (1) includes a blocking fluid guide element (7.1) and two connecting fluid guide elements (3, 4). The blocking fluid guide element (7.1) is connected in a fluid-tight manner to the two connecting fluid guide elements (3, 4). A clamping unit of the clamp (1) includes two clamping components (8.1, 10.1, 8.2, 10.2). The blocking fluid guide element (7.1) is located between the two clamping components (8.1, 10.1, 8.2, 10.2). In a releasing state of the clamping unit, the blocking fluid guide element (7.1) establishes a fluid connection between the two connecting fluid guide elements (3, 4). In a blocking state, the two clamping components (8.1, 10.1, 8.2, 10.2) prevent a flow of fluid through the blocking fluid guide element (7.1).

17 Claims, 10 Drawing Sheets

(51) Int. Cl.
*A61M 16/20* (2006.01)
*F16K 7/06* (2006.01)

(56) References Cited

U.S. PATENT DOCUMENTS

| | | | | |
|---|---|---|---|---|
| 2010/0280459 | A1 | 11/2010 | Werner | |
| 2015/0306329 | A1 | 10/2015 | Brown et al. | |
| 2019/0336718 | A1 | 11/2019 | Weikert et al. | |
| 2022/0241544 | A1* | 8/2022 | Fiorenza | F16K 1/36 |
| 2023/0181892 | A1* | 6/2023 | Ferreira Pasetto | A61M 39/284<br>604/539 |

FOREIGN PATENT DOCUMENTS

| | | | |
|---|---|---|---|
| EP | 3590572 | A1 | 1/2020 |
| WO | 2021191409 | A1 | 9/2021 |
| WO | 2021237325 | A1 | 12/2021 |

* cited by examiner 1
4
8.1
10.1
6.1
9.1
7.1
8.2
10.2
6.2
12.1
12.2
11.2
5.1
12.1
F
3
12.2
13
11.2
9.2

1
4
6.1
5.1
8.2
8.1
10.2
10.1
9.1
9.2
7.1
6.2
12.2
11.1
12.1
3
11.2
F 1
9.1
40.1
41.1
43.2
16.2
42.2
7.1
43.2
41.2
40.2
40.2
7.2
41.2
43.1
42.1
16.1
40.1
43.1
41.1
40.1

1
9.1
40.1
42.2
16.2
40.2
40.2
3
16.1
42.1
7.2

CLAMP, ESPECIALLY FOR A CONNECTION BETWEEN A VENTILATOR AND A PATIENT

CROSS REFERENCE TO RELATED APPLICATIONS

This application claims the benefit of priority under 35 U.S.C. § 119 of German Application 10 2022 101 528.9, filed Jan. 24, 2022, the entire contents of which are incorporated herein by reference.

TECHNICAL FIELD

The present invention pertains to a clamp, which is capable of selectively releasing or interrupting a fluid connection.

BACKGROUND

The clamp may be used, for example, as a part of a connection device, wherein the connection device at least temporarily establishes or is capable of establishing a fluid connection between a ventilator and a patient-side coupling unit. The patient-side coupling unit is arranged in or at or on the body of a patient and comprises, for example, a catheter or a tube or a breathing mask.

This patient shall be artificially ventilated by the ventilator. The ventilator carries out, as a rule, a sequence of ventilation strokes. A respective quantity of a gas mixture is conveyed during each ventilation stroke through the connection device to the patient-side coupling unit and flows into the body of the patient. This gas mixture comprises oxygen and optionally at least one anesthetic.

It may be necessary from time to time to interrupt this fluid connection, for example, in order to carry out maintenance or cleaning on the ventilator or in order to transport the patient from one ventilator to another ventilator. The lungs of the patient shall be prevented from being in a fluid communication with the surrounding area while the fluid connection to the ventilator is interrupted. This fluid communication with the surrounding area could cause the pressure in the lungs to drop and the lungs of the patient to collapse.

Various clamps for medical applications have become known.

A device, which comprises a fluid guide unit (dispositivos tubo, endotracheal tube 3), a clamp (clamp oclusor, occluder clamp 2), a seal (dispositivo de vedação, sealing device 1) for the fluid guide unit 3 and a connection element (conector 4) for a medical application, is described in WO 2021/237 325 A1. The fluid guide unit 3 can be passed through two recesses in the clamp 2. The clamp 2 comprises two jaws, which can be compressed and which thereby interrupt or at least restrict a flow through the fluid guide unit 3.

A fluid connection can be established between a ventilator (ventilator 115) and a patient-side coupling unit (patient interface 102) in EP 2 758 698 B1. This fluid connection comprises two fluid guide units (inspiratory breathing tube 103, return expiratory breathing tube 130). A clamp (locking tube clip 1) comprises two jaws (pair of jaws 4, each jaw 4 having a shoulder portion 10), which are connected to one another in an articulated manner. The two jaws 4 can be compressed and they then interrupt the fluid connection. A plurality of teeth (series of ridges, projections or teeth 11) on the jaws hold the two jaws 4 in the compressed state.

DE 10 2020 000 335 A1 shows a connection device, which establishes a fluid connection between a ventilator 17 and a patient-side coupling unit 26. The connection device comprises two breathing air hoses 18 and 21 as well as a valve device 1. A tubular rigid fluid guide unit 6 connects the patient-side connection 3 of the valve device 1 to the device-side connection 4. A shut-off unit 7 releases the fluid connection between the ventilator 17 and the patient-side coupling unit 26 in an open position and interrupts this fluid connection in a closed position. A locking unit 10 is capable of locking the shut-off unit 7 both in the open position and in the closed position.

A fluid connection between a ventilator (ventilator) and a patient-side coupling unit (catheter 106 for oxygenation of a patient—endotracheal tube 113 placed in the trachea 102 of a patient 103), which comprises a ventilator connector 107 on the patient side and an adapter 109 on the device side, is described in US 2015/0 306 329 A1. The catheter 106 is inserted into a tube (main body 213 of the adapter 214). A valve (throttling valve 309 in the interior region 201 of the hollow main body 213) can be adjusted in order to change the flow of fluid through the tube 213.

SUMMARY

A basic object of the present invention is to provide a clamp, which is capable of selectively releasing or blocking a fluid connection, and which can be used with a higher level of operational reliability than prior-art clamps of this kind.

The object is accomplished by a clamp having features according to the invention and a process having features according to the invention. Advantageous embodiments are described in this disclosure.

The term “fluid” is a generic term for gases and liquids and other free-flowing substances.

The term “fluid guide element” will hereinafter be used. A fluid guide element is to be understood as a component which is capable of guiding a fluid, especially a gas or gas mixture, along a predefined trajectory and which ideally prevents the fluid from leaving this trajectory. The fluid guide unit may be rigid or flexible, and it may be especially a rigid tube or a flexible hose, also a two-lumen hose. The fluid guide unit may also comprise a combination of at least one rigid element and of at least one flexible element. The term “fluid guide unit” has the same meaning.

In addition, the notion of establishment of a fluid connection between two components or devices will be used below. This notion is defined such that a fluid can flow from one component/device to the other component/device, ideally without leaking into the surrounding area. It is possible that the two components/devices are connected directly to one another. It is also possible that a distance between the two components/devices occurs and a fluid guide element or unit, for example, a hose, connects the two components/devices to one another. It is possible that a fluid flows from time to time from the first component/device through the fluid connection to the second component/device and from time to time in the opposite direction from the second component/device through the fluid connection to the first component/device. The fluid connection may be established permanently or only from time to time.

The clamp according to the present invention is capable of selectively releasing or blocking a fluid connection between two devices.

The clamp according to the present invention comprises a clamping tube. The clamping tube comprises a blocking fluid guide element, a first connecting fluid guide element and a second connecting fluid guide element. The fluid connection between the two devices passes through the clamp and is passed through the blocking fluid guide element and through the two connecting fluid guide elements. The blocking fluid guide element is connected to both connecting fluid guide elements in a fluid-tight manner, for example, by a connection in substance or by a positive-locking or non-positive connection. The feature "fluid-tight" does not rule out the formation of inevitable gaps due to construction-related causes or in the course of use.

The clamp according to the present invention comprises, furthermore, a clamping unit with two clamping components. The two clamping components are, for example, two jaws. The blocking fluid guide element is located between the two clamping components. At least one clamping component, preferably both clamping components can be moved relative to the blocking fluid guide element. The two clamping components can be moved especially preferably towards one another and away from one another.

The clamping unit can selectively be transferred (brought) into a releasing state or into a blocking state (blocked state, clamping state).

When the clamping unit is in the releasing state, the blocking fluid guide element establishes a fluid connection between the two connecting fluid guide elements. The clamping unit releases this fluid connection.

When the clamping unit is in the blocking state, the two clamping components prevent a flow of fluid through the blocking fluid guide element. The two clamping components prevent or at least reduce a flow of fluid through the blocking fluid guide element by at least 80%, preferably by at least 90% and especially preferably by at least 95% compared to the releasing state. As a result, the clamping unit in the blocking state interrupts a fluid connection between the two connecting fluid guide elements or it at least relevantly limits this fluid connection.

Some fluid may frequently still flow based on inevitable gaps even if a flow of fluid is interrupted. The cross-sectional area through the blocking fluid guide element is smaller with the clamping unit being in the blocking state than in the releasing state and in one embodiment it equals zero in the blocking state. When the clamping unit is in the blocking state, the two clamping components together prevent and interrupt this fluid connection or at least reduce the maximum possible flow rate through the fluid connection.

According to the present invention, the fluid connection between the two connecting fluid guide elements is passed through the blocking fluid guide element. To interrupt the fluid connection, it is sufficient to move the clamping unit into the blocking state and to interrupt thereby the flow of fluid through the blocking fluid guide element. It is not necessary to influence a connecting fluid guide element.

As a rule, during a productive use of the clamp at least one connecting fluid guide element is connected to a fluid guide unit, for example, to a hose, which fluid guide unit leads to a patient-side coupling unit. The feature according to the present invention with the clamping unit eliminates the need to place a clamp or a plug or another closure on the connected fluid guide unit or on a connected fluid guide unit when the fluid connection shall be interrupted. In addition, the present invention eliminates the need to separate the connected fluid guide unit at a point and to place a plug or another closure on the separation point. Such a closure may at times be unavailable when it is needed. The attachment of the closure may lead to a contamination or infection of the fluid connection. In addition, the risk of development of a leak at the separation point is greater than in case of the use of the clamp according to the present invention.

In many cases, thanks to the present invention a fluid connection between two devices, for example, between a ventilator and a patient-side coupling unit, can be interrupted rapidly and later restored. It is sufficient to compress the two clamping components and thereby to bring the clamping unit into the blocking state and to pull them apart again or release them later and bring the clamping unit thereby into the releasing state or to make it possible for the clamping unit to change over by itself into the releasing state, for example, by the force of a resetting spring.

In particular, the clamp according to the present invention can therefore be used to separate a patient from a ventilator and to connect him/her later again to the same ventilator or to another ventilator. While the patient is separated from the ventilator, the ventilator is, for example, cleaned or disinfected or is supplied with additional operating materials or maintenance or repair is carried out on it. Or else, the patient is transported from one ventilator to another ventilator. It is not necessary to separate or to remove the patient-side coupling unit from the patient. The patient-side coupling unit rather remains in or at or on the body of the patient, and the clamp remains directly or indirectly connected to the patient-side coupling unit.

The clamping unit of the clamp according to the present invention acts mechanically on the clamping tube and hence on the fluid connection only from outside. This reduces the risk of contaminants, germs, or other particles being introduced or entering into the fluid connection when the fluid connection is interrupted.

According to the present invention, the clamping tube comprises a blocking fluid guide element and two connecting fluid guide elements. Thanks to this feature, a distance develops between

- the area in which the two clamping components of the clamping unit act on the blocking fluid guide element and
- the area in which the clamp according to the present invention can be connected to a fluid guide unit.

As a result, the clamping unit does not influence a fluid guide unit, which is connected to the clamp. Such an influence could lead to a leak and/or to damage or to swirling in a fluid flow.

In many cases, the present invention does not lead to an additional relevant dead space in the fluid connection between the two connected devices. The clamping tube can be configured such that it has only a relatively small volume. Such a dead space is frequently undesired, especially because a dead space may slow down the flow of fluid to and from the patient. In addition, such a relevant dead space may lead to undesired swirling. When the clamping unit is in the releasing state, ideally it does not affect the flow of fluid from the one device to the other device.

The clamping tube may be configured as a straight or bent tube without corners and edges and bends, so that the risk of swirling in the clamping tube or of the depositing of impurities or germs in the interior of the clamping tube is low.

The entire clamp according to the invention may be embodied as a passive mechanical component. The position of the two clamping components relative to one another indicates in an intuitive and rapidly perceptible manner whether the fluid connection is currently established or is interrupted by the clamp, even in case of poor light conditions. A separate sensor is not necessary.

The entire clamp may be manufactured from materials that meet the requirements imposed on a medical device, for example, partly from a rigid plastic and partly from a flexible plastic, the requirements pertaining especially to the cleaning and to the disinfection of the clamp.

In a preferred embodiment, the two connecting fluid guide elements are two rigid tubular components. This embodiment makes it easier in many cases to connect a connecting fluid guide element to a fluid guide unit. The fluid guide unit is, for example, an elastic hose, which is pushed or pulled over the rigid connecting fluid guide element, or else the fluid guide unit is detachably connected to the connecting fluid guide element by means of a screw connection or a snap-in connection.

Each clamping component is preferably mechanically connected to a respective rigid connecting fluid guide element. Both clamping components are preferably connected mechanically to the same connecting fluid guide element. It is also possible that the two clamping components are connected mechanically to two different connecting fluid guide elements.

In a preferred embodiment, the two connecting fluid guide elements are permanently mechanically connected to one another by at least one mechanical connection element, preferably by two connection elements located at spaced locations from one another. This embodiment leads to a further increase in the mechanical stability of the clamp. The connection element or each connection element is preferably arranged outside of the blocking fluid guide element.

According to the present invention, the blocking fluid guide element connects the two connecting fluid guide elements with each other in a fluid-tight manner. The blocking fluid guide element may be a rigid tubular component. In a preferred embodiment, the blocking fluid guide element is, by contrast, flexible over its entire length or in at least one area, i.e., it can be compressed or squeezed in a reversible manner. It is possible that this flexible blocking fluid guide element connects the two connecting fluid guide elements directly to one another. In one embodiment this flexible blocking fluid guide element is manufactured from a hose.

When the clamping unit is in the blocking state, the two clamping components clamp or pinch the blocking fluid guide element between them according to this preferred embodiment, doing so in the flexible area. Due to the clamping or pinching, the clamping unit interrupts the flow of fluid through the blocking fluid guide element or at least it reduces this flow by at least 80%. When the clamping unit is in the releasing state, preferably a distance develops between the blocking fluid guide element and the clamping unit so that the blocking fluid guide element will not be clamped in that case.

In an implementation of this embodiment, the two clamping components comprise a jaw each or they are configured each as a jaw. These two jaws are connected to one another, preferably in an articulated manner in the manner of a V or a U. It is also possible that one jaw can be linearly moved or shifted relative to the other jaw. Each jaw belongs to a respective clamping component. When the clamping unit is in the blocking state, the two jaws clamp or pinch the blocking fluid guide element between them, doing so in the flexible area thereof. When the clamping unit is in the releasing state, preferably a respective distance occurs between the blocking fluid guide element and the two jaws.

In one embodiment, the clamp comprises two guiding elements. A respective guiding element of the clamp is associated with each jaw. For example, the jaw is passed through two webs of the guiding element. Each guiding element is capable of guiding the associated jaw, while the jaw is moved relative to the clamping tube. Such a movement occurs especially when the clamping unit is transferred from one state into the other state.

In one embodiment, the one guiding element has an elongated hole. The other guiding element comprises a fork. In both states of the clamping unit, the clamping tube is guided through the elongated hole. As a result, the maximum possible distance between this jaw and the clamping tube is limited. When the clamping unit is in the blocking state, the fork encloses the clamping tube from two sides. As a result, a lateral movement of the jaw relative to the clamping tube is limited.

According to an embodiment described above, each clamping component comprises a jaw each. According to another embodiment, each clamping component comprises a respective blocking slider. Each blocking slider can be moved relative to the blocking fluid guide element between two end positions, namely between a blocking position and a releasing position. The clamping unit is in the blocking state when the two blocking sliders are in the blocking position. The two blocking sliders together then prevent or reduce a fluid connection through the blocking fluid guide element. When both blocking sliders are in the releasing position, the clamping unit is in the releasing state.

It is possible to combine the embodiment with the jaws with the embodiment with the blocking slider. This combination generates redundancy and increases the operational reliability.

In one embodiment, the one blocking slider can be moved independently from the other blocking slider from one position into the other position. Hereby it is possible to restrict the flow of fluid through the blocking fluid guide element, for example, by 50% compared to the releasing state, without completely interrupting the flow. In another embodiment, the two blocking sliders are mechanically coupled with one another, so that they can only be moved synchronously with one another and therefore either both blocking sliders are in the blocking position or both blocking sliders are in the releasing position.

The embodiment with the two blocking sliders is preferably combined with an embodiment in which the blocking fluid guide element is configured as a rigid tubular component. The embodiment with the two blocking sliders may also be connected to a flexible blocking fluid guide element.

According to the present invention, the clamping unit can be brought into a blocking state. In a preferred embodiment, the clamp comprises a locking unit. This locking unit is capable of detachably locking the two clamping components. The locking unit is preferably capable of locking the two clamping components at least when the clamping unit is in the blocking state. As a result, the locking unit holds the clamping unit in the blocking state and prevents the clamping unit from unintentionally being moved into the releasing state or from moving by itself into the releasing state. Such an unintended releasing state can cause a fluid communication to be established between the lungs of a patient and the surrounding area, which is often undesirable.

It is also possible that additionally or instead of this, the locking unit is capable of locking the clamping components such that the clamping unit is thereby held in the releasing state. In this embodiment the locking unit prevents the clamping unit from being unintentionally brought into the blocking state. Bringing into the blocking state is undesired, for example, during artificial ventilation, because the fluid connection between the ventilator and the patient-side coupling unit is thereby interrupted during artificial ventilation.

It is also possible that the locking unit is, in addition, capable of locking the two clamping components in an intermediate state between the releasing state and the blocking state. The clamping unit causes in many cases in the intermediate state the cross section of a fluid connection to be reduced by the clamp compared to the releasing state, but the cross section of the fluid connection is not reduced completely to zero compared to the blocking state. This embodiment often leads to reduced pressure in the clamping tube between the two clamping components, which in many cases reduces the volume flow and facilitates a measurement of the volume flow in some cases.

In one embodiment, the distance between the two clamping components can be changed, for example, by compressing the two clamping components against the force of a spring and by the spring configured to push the two clamping components away from one another again. When the clamping unit is in the blocking state, the distance between the two clamping components is shorter than the distance that is present when the clamping unit is in the releasing state. The locking unit is configured to lock the two clamping components in a state of the shorter distance or shortest distance from one another.

In one embodiment, the locking unit is capable of locking the two clamping components in a state in which the two clamping components have a minimal distance from each other. This embodiment can be achieved with a relatively small locking unit. In addition, this embodiment embodies in many cases the locking unit in an especially simple manner. It is in many cases obvious and intuitive for a user to realize how the locking can be established and/or eliminated again between the two clamping components.

In one implementation, the locking unit comprises two holders and two holding elements. A respective holder is attached to each clamping component. A respective holding element is attached to each holder. When the clamping unit is in the blocking state, one holding element is connected detachably to the other holding element. In particular, the one holding element meshes with the other holding element. As a result, the two clamping components are detachably connected to one another. In order to bring the clamping unit from the blocking state into the releasing state, the two holding elements must be separated from one another. Preferably a spring moves the two unlocked clamping components away from one another. The embodiment implements the locking unit in an especially simple manner. How the clamping components are to be brought into the releasing state is obvious and intuitive to a user.

It is possible that the two holding elements also act as the guiding elements.

The clamp according to the present invention can be used as a component of a connection device. This connection device establishes permanently or at least from time to time a fluid connection between a first device, e.g. a patient-side coupling unit, and a second device, e.g. a medical device, and/or is capable of establishing such a fluid connection at least from time to time. The patient-side coupling unit is positioned in or at or on or at the body of a patient. The medical device is preferably a ventilator, which conveys a fluid, especially a gas mixture containing oxygen, to the patient-side coupling unit and thereby carries out artificial ventilation of the patient.

A “ventilator” is defined as a device that is capable of supplying a patient-side coupling unit and hence a patient with a gas mixture. This gas mixture comprises oxygen and may comprise at least one anesthetic. The ventilator causes this gas mixture to be conveyed or delivered to the patient-side coupling unit. The ventilator carries out, as a rule, a sequence of ventilation strokes and causes a respective quantity of the gas mixture to be conveyed to the patient-side coupling unit during each ventilation stroke. In one application, the ventilator supports the intrinsic breathing activity of the patient. In case of a supportive artificial ventilation, the ventilation strokes are preferably synchronized with the intrinsic breathing activity of the patient. In another application, the patient is fully anesthetized. It is possible that this gas mixture additionally comprises at least one anesthetic in order to anesthetize or sedate the patient.

In one embodiment, the clamp according to the present invention—or at least the rigid components of the clamp—are or can be manufactured by means of a 3D printer. The 3D printer comprises a processor and a memory. A computer program is stored in the memory. The processor is capable of reading the computer program from the memory and of executing the computer program.

During the execution of the computer program, the processor actuates the 3D printer. The actuation of the 3D printer causes the actuated 3D printer to print the entire clamp according to the present invention or at least the rigid components of the clamp. In order to enable a 3D printer known from the state of the art to print the clamp or at least the rigid components, it is sufficient correspondingly to adapt the computer program and, of course, to provide the 3D printer with the necessary raw material. The 3D printer does not, as a rule, need to be adapted beyond this.

The present invention further pertains to a connection device, which from time to time establishes or is at least capable of establishing a fluid connection between a first device and a second device. This connection device comprises at least one clamp according to the present invention as well as a first fluid guide unit and a second fluid guide unit. The first fluid guide unit is connected to the first device, the second fluid guide unit is connected to the second device. The first connecting fluid guide element is at least from time to time connected in a fluid-tight manner to the first fluid guide unit of the clamp according to the present invention. The second connecting fluid guide element is at least from time to time connected in a fluid-tight manner to the second fluid guide unit. The clamp according to the present invention is consequently capable of selectively releasing or blocking a fluid connection between the first device and the second device, this fluid connection passing through the two fluid guide units and the clamping tube. It is possible that two clamps are connected in series, in which case at least one clamp is configured as a clamp according to the present invention, optionally both clamps. In many cases, this embodiment generates redundancy.

The present invention further pertains to a ventilation system with a connection device according to the present invention. The ventilation system comprises, in addition, a ventilator and a patient-side coupling unit. The patient-side coupling unit acts as the first device, and the first fluid guide unit of the connection device is connected to the patient-side coupling unit in a fluid-tight manner or can be connected in a fluid-tight manner. The ventilator acts as the second device, and the second fluid guide unit of the connection device is at least temporarily connected to the ventilator in a fluid-tight manner or can be connected in a fluid-tight manner.

When the first fluid guide unit is connected to the patient-side coupling unit and the second fluid guide unit is connected to the ventilator, a fluid connection is established or can be established, and this fluid connection extends through the two fluid guide units and through the clamping tube of the clamp. When the clamping unit is in the releasing state, it releases this fluid connection. When the clamping unit is in the blocking state, the clamp completely interrupts the fluid connection or at least reduces the flow rate that can be reached through this fluid connection compared to the releasing state.

The first connecting fluid guide element is preferably connected permanently to the first fluid guide unit. The first fluid guide unit is, in turn, permanently connected to the patient-side coupling unit. As a result, the first connection fluid guide element is also connected permanently to the patient-side coupling unit. The patient-side coupling unit and, as a result, the lungs of the patient are prevented from unintentionally coming into fluid communication with the surrounding area. This could lead to a vacuum in the lungs and put the health of the patient at risk. As long as the clamping unit is in the blocking state, the clamp prevents fluid communication between the patient-side coupling unit and hence the lungs of the patient, on the one hand, and the surrounding area, on the other hand.

Preferably the second connecting fluid guide element is detachably connected to the second fluid guide unit. As a result, the same patient can be connected first to a first ventilator and then to a second ventilator, without the clamp needing to be separated from the patient-side coupling unit in between.

The present invention will be described below on the basis of an exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

Figure 8:
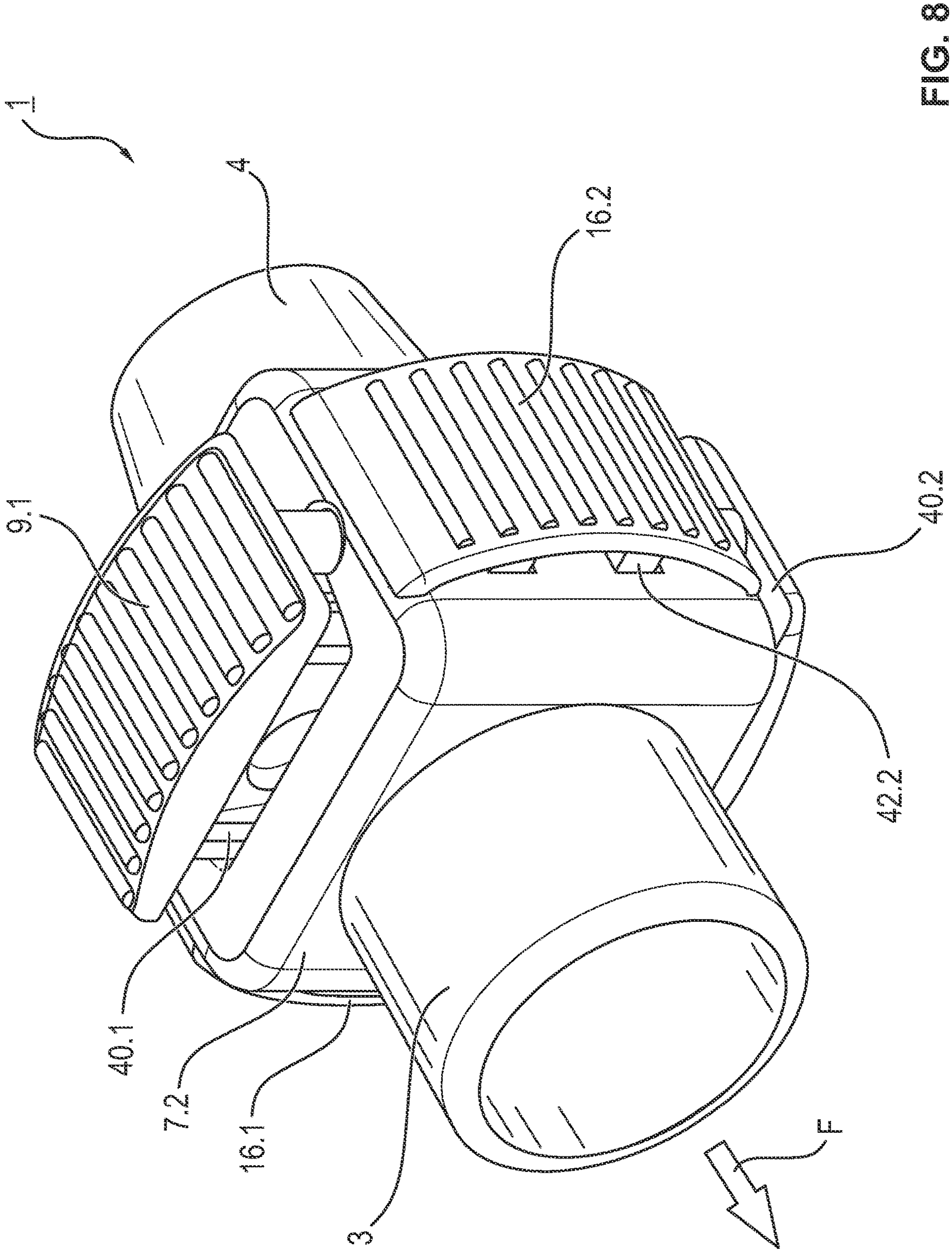
FIG. 8 is a perspective view showing a third embodiment of the clamp according to the present invention in the releasing state.
Figure 10:
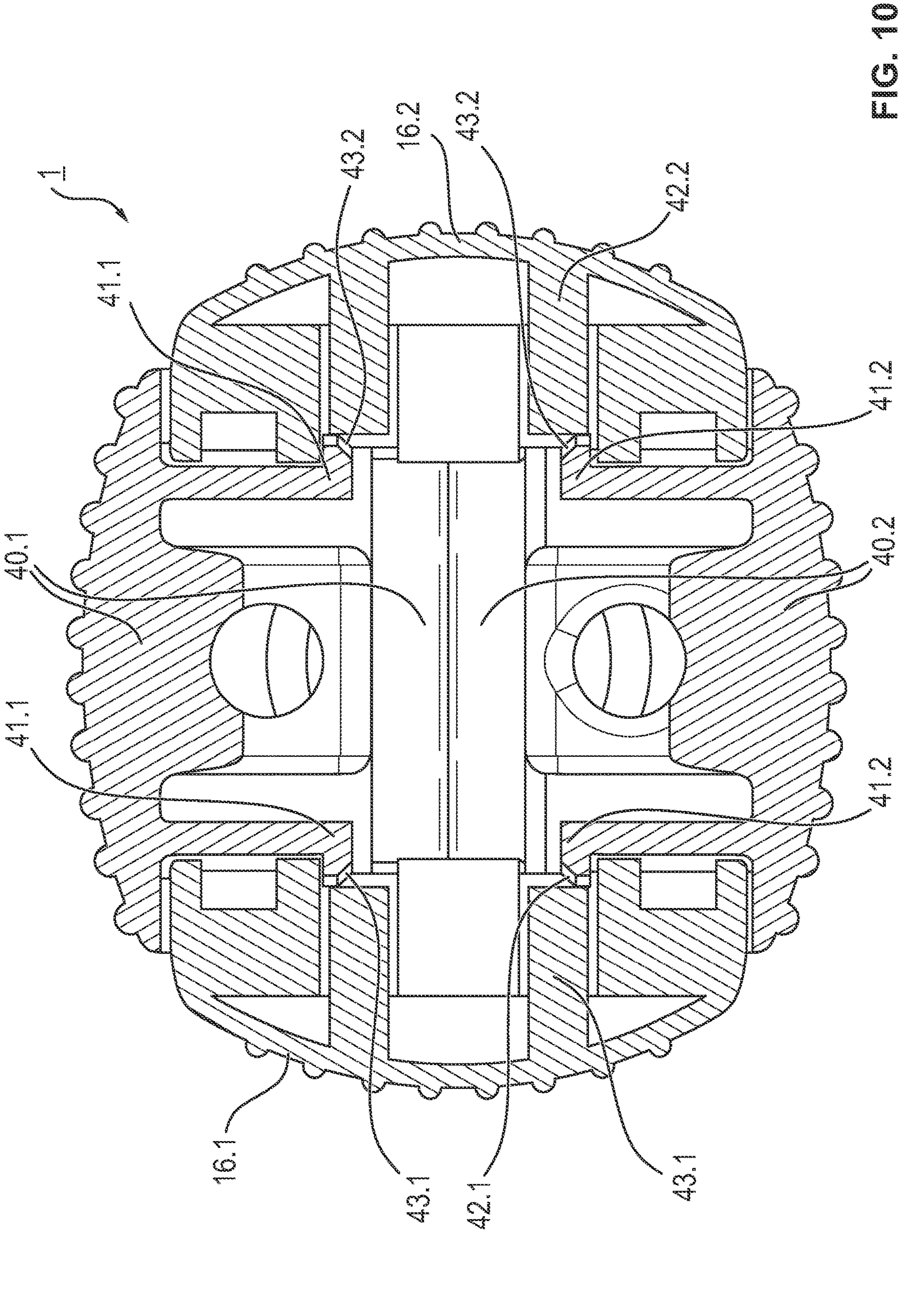

FIG. **9*a* is a front view showing the third embodiment according to FIG. 8** in the releasing state;

FIG. **9*b* is a sectional view showing the third embodiment according to FIG. 8 in the releasing state; and FIG. 10 is a sectional view showing the third embodiment according to FIG. 8** in the blocking state.

DESCRIPTION OF PREFERRED EMBODIMENTS

Referring to the drawings, the present invention is used in the exemplary embodiment for the artificial ventilation of a patient. A patient-side coupling unit is arranged in or at or on the body of the patient. The patient-side coupling unit comprises, e.g., a ventilation tube, a breathing mask and/or a mouthpiece. A fluid connection is established between the patient-side coupling unit and a ventilator. A gas mixture can flow through this fluid connection from the ventilator to the patient-side coupling unit. Two fluid connections are optionally established, so that a gas mixture can flow back from the patient-side coupling unit to the ventilator.

The ventilator carries out a sequence of ventilation strokes in order to feed a gas mixture containing oxygen to the patient through the fluid connection. The gas mixture may contain at least one anesthetic in order to anesthetize or at least sedate the patient.

Figure 1:
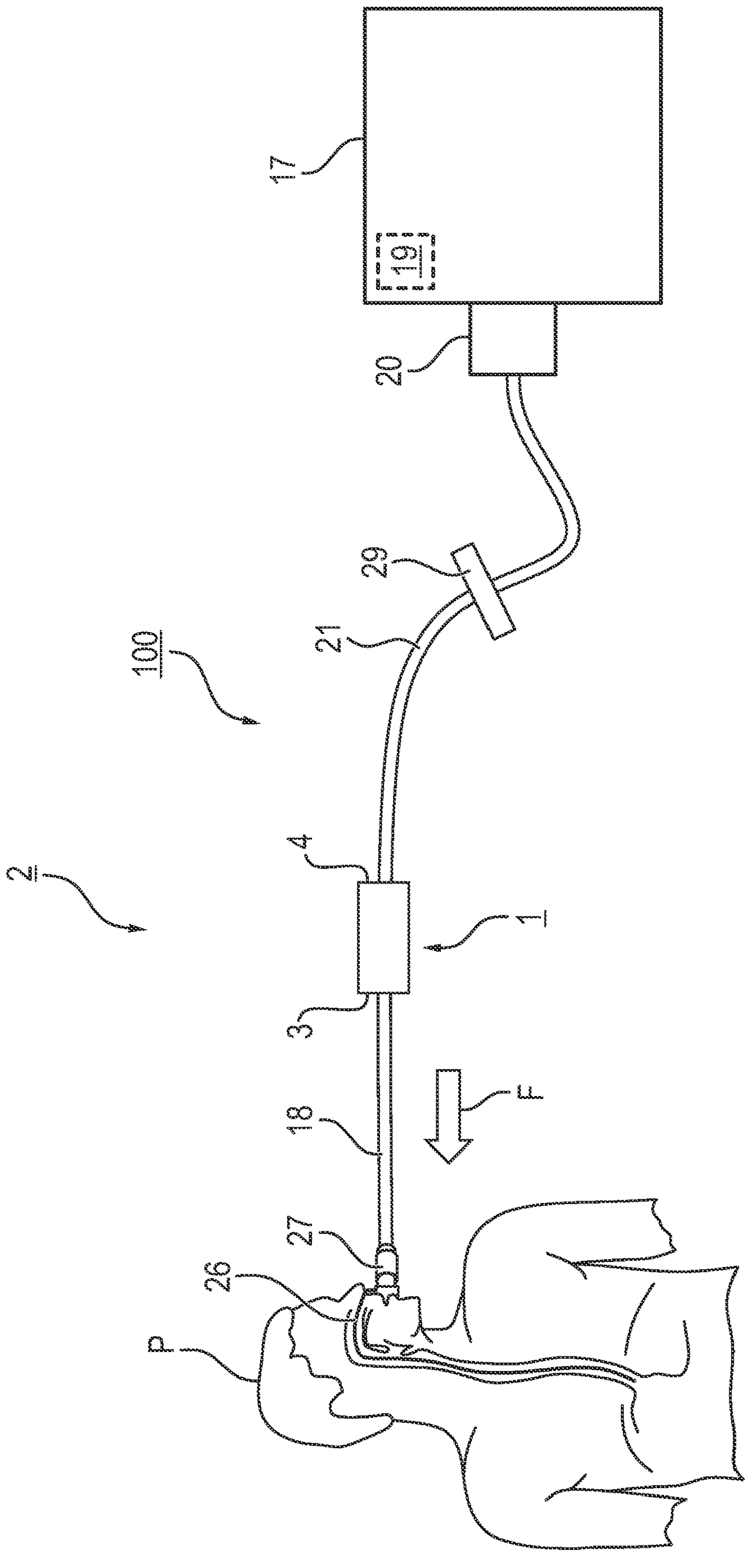
FIG. 1 is a schematic view showing a ventilation device for the artificial ventilation of a patient by means of a ventilator.

FIG. 1 schematically shows a ventilation system 2, which ventilates a patient P mechanically and comprises the following components:

- a ventilator 17 with a display and operating unit 19 shown schematically and with a fluid delivery unit, not shown, for example, a blower or a pump,
- a patient-side coupling unit comprising an endotracheal tube or a tracheal cannula or a catheter 26,
- a mouthpiece 27, which is connected to the component 26 in a fluid-tight manner,
- a patient-side hose system 18, which is connected to the patient-side coupling unit 26,
- a device-side hose system 21, which is connected to the ventilator 17,
- an optional breathing air filter 20 between the device-side hose system 21 and the ventilator 17,
- an optional filter 29 against bacteria, microbes, and viruses, wherein the filter 29 is preferably arranged in the device-side hose system 21, and
- a clamp 1 according to the present invention between the two hose systems 18 and 21, wherein the clamp 1 will be explained in more detail below.

In the embodiment shown in FIG. 1, the clamp 1 is connected to the hose system 18 in a fluid-tight manner, and the hose system 18 is connected to the mouthpiece 27 in a fluid-tight manner. Gaps may, of course, occur based on inevitable deviations between actual and desired states and changes in the materials used.

It is also possible that the clamp 1 is connected directly to the mouthpiece 27 or to the tube or catheter 26 or to another component of the patient-side coupling unit. In one embodiment, the clamp 1 and the mouthpiece 27 form a single component. This component 1, 27 is connected or can be connected to the tube or catheter 26 and to the device-side hose system 21 in a fluid-tight manner.

The flow direction, in which a gas mixture flows from the ventilator 17 through the fluid connection to the patient-side coupling unit 26, is suggested by the arrow F in FIG. 1.

It is necessary in many cases from time to time to interrupt the fluid connection between the ventilator 17 and the patient-side coupling unit 26. A possible reason on the patient side is that the patient P shall be transported from the ventilator 17 to another ventilator. Possible device-side reasons for interrupting the fluid connection are that a cleaning or maintenance or repair must be carried out on the ventilator 17 or that an operating material, especially a filter element, must be replenished or replaced. As soon as and as long as the fluid connection is interrupted, the patient P is separated from the ventilator 17. The patient is thus disconnected from the artificial ventilation from time to time. The time period during which the patient P is disconnected from the artificial ventilation is usually shorter than 3 minutes. Without countermeasures, there would be in many cases a risk that the patient-side coupling unit 26 and hence the lungs of the patient P is/are in a fluid communication with the surrounding area when the fluid connection between the patient P and the ventilator 17 is interrupted. Such a fluid communication with the surrounding area is often undesired since it may lead to a drop in the residual air pressure in the lungs of the patient P (end-expiratory pressure, PEEP). This could cause in some patients a collapse of the lungs or the development of an atelectasis. The clamp 1 according to the present invention reduces the risk of occurrence of an undesired fluid communication between the lungs and the surrounding area, and it thus reduces the risk of an undesirably low end-expiratory pressure. The clamp 1 rather contributes in many cases to an interruption of the fluid communication and thus to the maintenance of a residual air pressure (PEEP) in the lungs for a sufficiently long time.

Figure 2:
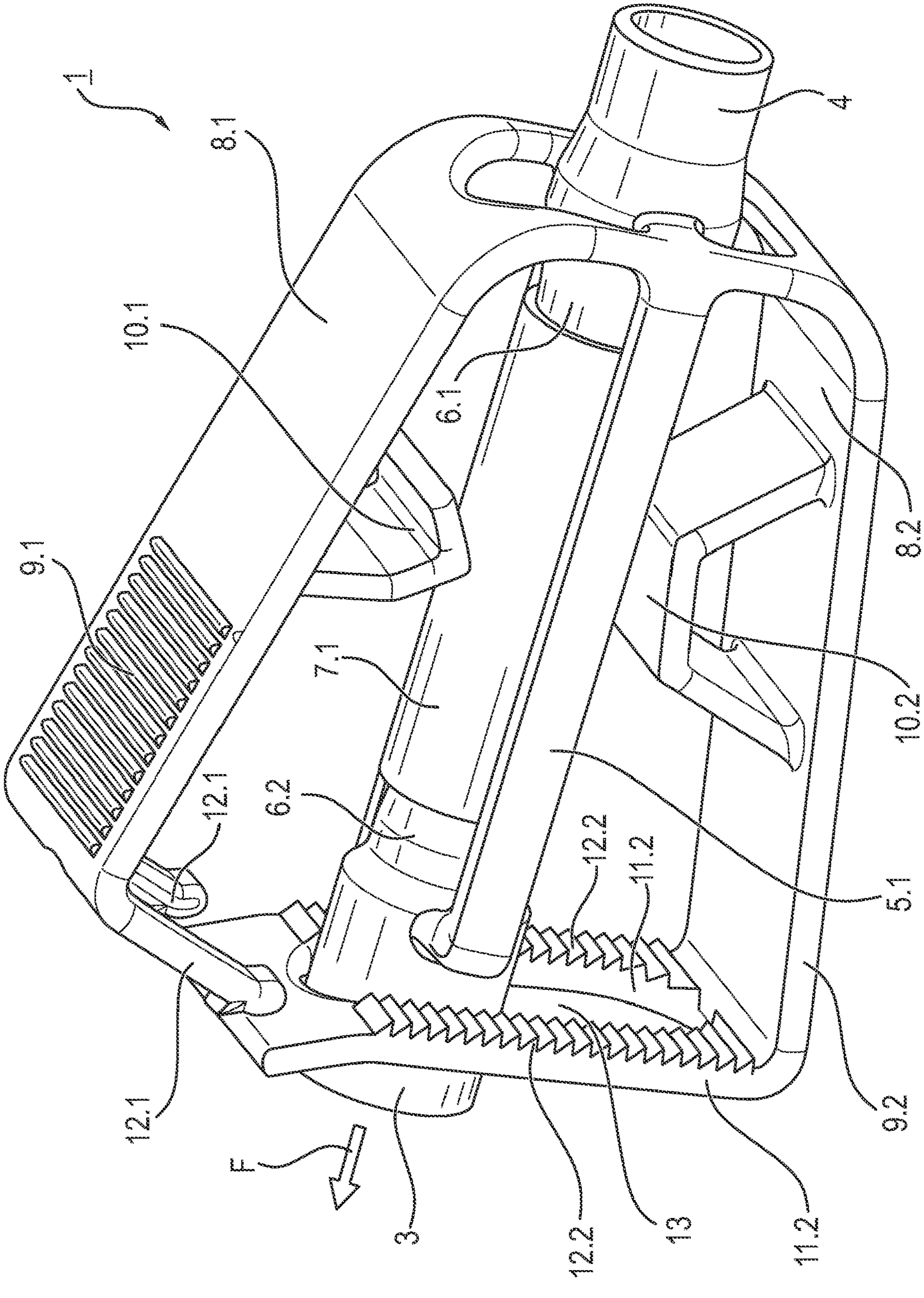
FIG. 2 is a perspective view showing a first embodiment of the clamp according to the present invention in the releasing state.
Figure 3:
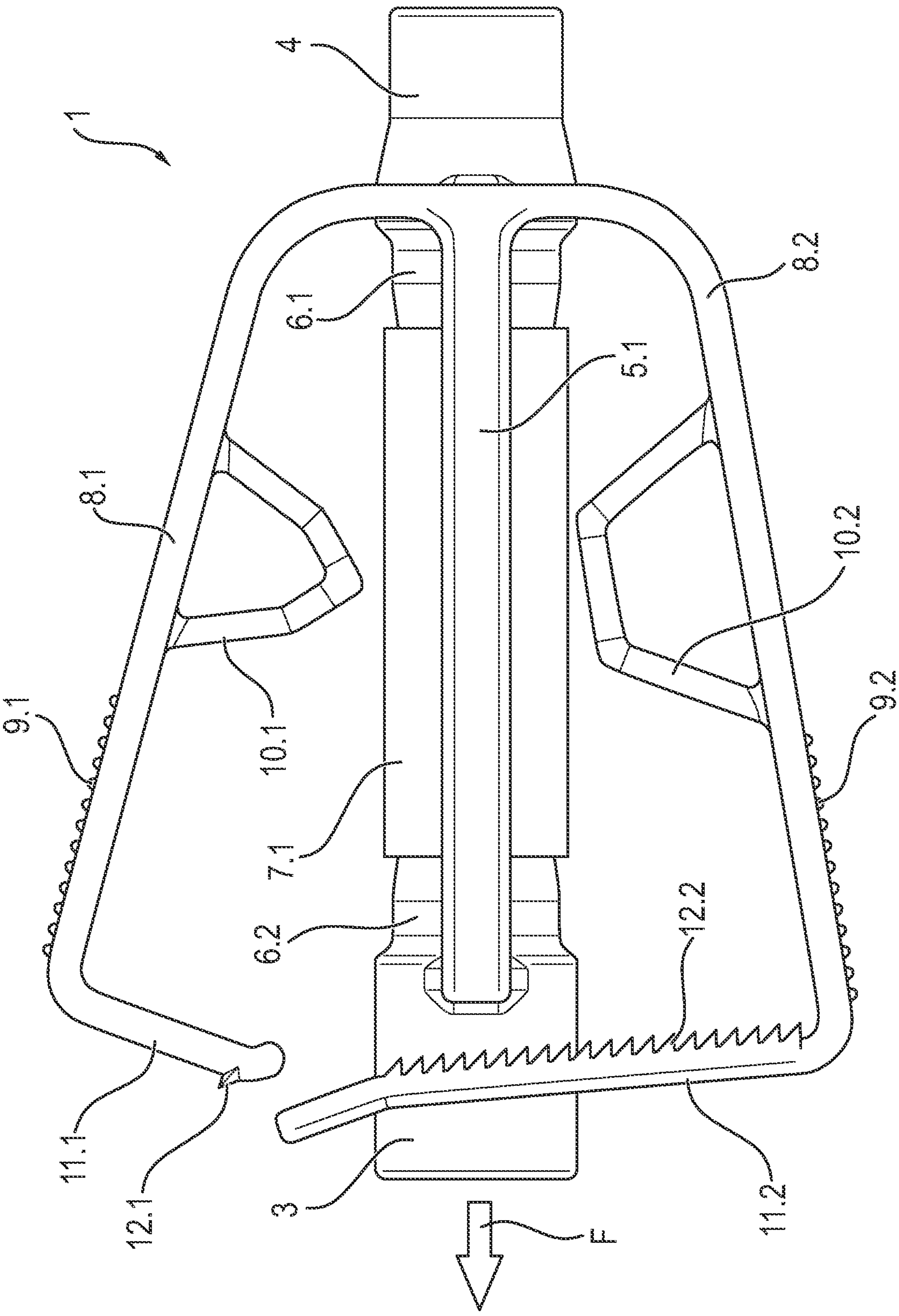
FIG. 3 is a side view showing the first embodiment according to FIG. 2 in the releasing state.
Figure 4:
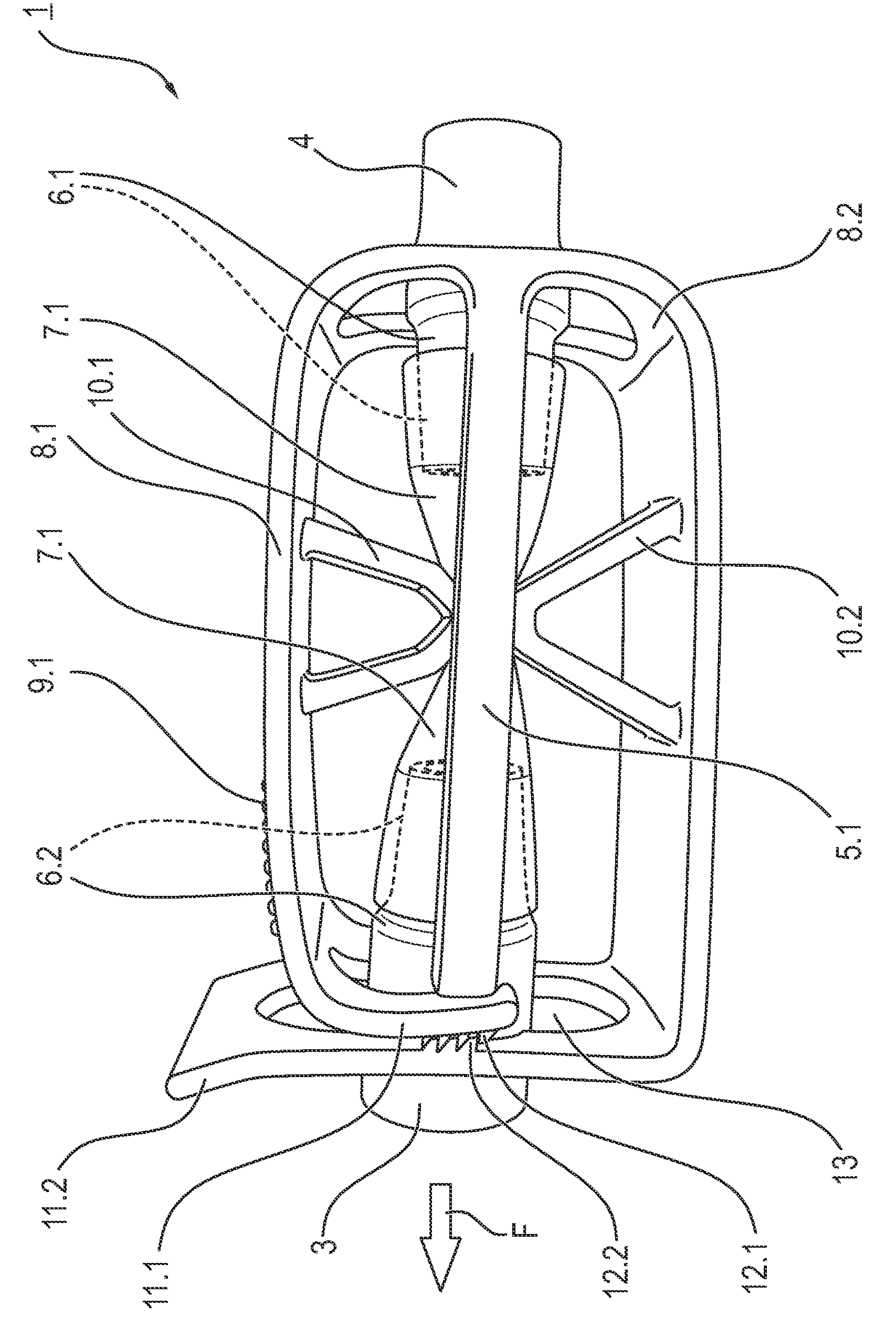
FIG. 4 is a side view showing the first embodiment according to FIG. 2 in the blocking state.

FIG. 2, FIG. 3, and FIG. 4 show the clamp 1 according to a first embodiment of the exemplary embodiment in two perspective views and in a side view. The clamp 1 comprises a patient-side connecting fluid guide element 3 and a device-side connecting fluid guide element 4. The two connecting elements 3, 4 act as the two connecting fluid guide elements. The patient-side connecting element 3 is connected to the patient-side hose system 18 in a fluid-tight manner, preferably permanently, and optionally detachably. The device-side connecting element 4 is detachably connected to the device-side hose system 21 in a fluid-tight manner. The two connecting elements 3, 4 each comprise a hollow cylinder and a hollow cone 6.1, 6.2, which is permanently connected to the cylinder. The free closing surfaces of the two cones 6.1, 6.2 face one another. Two webs 5.1, 5.2, which extend parallel to the flow direction F, connect the two connecting elements 3, 4 permanently to one another and act as mechanical connection elements.

A hose 7.1 is pulled over the two cones 6.1, 6.2. This hose 7.1 is manufactured from a flexible material, i.e., it can be deformed reversibly and especially by pushing in, and is connected to the two cones 6.1, 6.2

- by connection in substance, for example, by a bonded connection,
- in a positive-locking (form-fit) manner, for example, by the intrinsic elasticity, and/or
- in a force-locked manner, for example, by means of a circumferential projection, and it embodies a fluid-tight fluid connection between the two connecting elements 3 and 4. The hose 7.1 forms the blocking fluid guide element in the first embodiment.

A gas mixture, which flows from the ventilator 17 to the patient-side coupling unit 26 in the flow direction F, flows through the device-side hose system 21, the connecting element 4, the hose 7.1, the connecting element 3, and the patient-side hose system 18.

The two connecting elements 3 and 4 with the cones 6.1 and 6.2, the webs 5.1 and 5.2 as well as the hose 7.1 belong to the clamping tube according to the first embodiment.

The two connecting elements 3 and 4 as well as the two webs 5.1 and 5.2 are preferably manufactured from a solid plastic, while the hose 7.1 is flexible and can be reversibly compressed. All these components are manufactured each from a material that has a sufficient resistance to detergents and disinfectants. The hose 7.1 is preferably manufactured from silicone. The two webs 5.1 and 5.2 prevent the one connecting element 3, 4 from being able to move relative to the other connecting element 4, 3. Therefore, and since the hose 7.1 is pulled over the two cones 6.1, 6.2 or is connected to them in another manner, the risk of bending or kinking of the hose 7.1 is relatively low. The risk of the hose 7.1 being damaged or pulled unintentionally from a connecting element 3, 4 is therefore relatively low. Furthermore, the risk that the clamp 1 leads to a leak in the fluid connection is relatively low.

When the hose 7.1 is fully compressed, practically no fluid can flow through the hose 7.1, and the fluid connection between the two connecting elements 3 and 4 is interrupted. Since the clamp 1 is connected in a fluid-tight manner to the patient-side hose system 18, a fluid communication between the lungs of the patient P and the surrounding area is prevented from occurring.

The clamp 1 comprises a clamping unit with two jaws 8.1 and 8.2, wherein the two jaws 8.1 and 8.2 enclose the hose 7.1 from two opposite sides. The two jaws 8.1 and 8.2 are connected to the two webs 5.1 and 5.2 in an articulated manner and are connected to one another in an articulated manner in the form of a V, namely, at the level of the device-side connecting element 4. The two jaws 8.1, 8.2 are also connected via the webs 5.1, 5.2 to the device-side connecting element 4. The jaws 8.1, 8.2 can be rotated relative to the two webs 5.1, 5.2 about an axis of rotation DA, which axis extends through the device-side connecting element 4. It is also possible that the axis of rotation DA passes through the patient-side connecting element 3 and the two jaws 8.1, 8.2 are connected to the patient-side connecting element 3 in an articulated manner.

A gripping element 9.1, 9.2 each in the form of a fluting is arranged on the outwardly pointing surface of one of the jaws 8.1, 8.2. A respective V-shaped clamping element 10.1, 10.2 with a rounded tip, which tip points towards the hose 7.1, is attached to the inwardly pointing surface.

FIG. 2 and FIG. 3 show a releasing state of the clamping unit 8.1, 8.2. In this releasing state the two jaws 8.1 and 8.2 have the maximum possible distance from one another and release the hose 7.1, so that the fluid connection is established between the two connecting elements 3 and 4. The distance between the two clamping elements 10.1 and 10.2 is greater in the releasing state than the diameter of the non-compressed hose 7.1. The two clamping elements 10.1 and 10.2 thus do not hinder the flow of a fluid through the hose 7.1.

The two jaws 8.1 and 8.2 can be compressed until the two clamping elements 10.1, 10.2 compress the hose 7.1 completely and the two jaws 8.1 and 8.2 have the minimal distance from one another, cf. FIG. 4. The two jaws 8.1 and 8.2 and hence the clamping unit are in a blocking state at the minimal distance and interrupt the fluid connection between the two connecting elements 3 and 4. The two clamping elements 10.1 and 10.2 clamp especially the hose 7.1 between them and compress it in the blocking state, so that the fluid connection is interrupted. However, the flow rate, which is still possible through the hose 7.1, is reduced at least to less than 20%, preferably to less than 10% and especially preferably to less than 5% of the flow rate occurring in the releasing state. The flow rate is reduced to 0% in case of an interrupted fluid connection.

When the jaws 8.1, 8.2 are in this blocking state, the device-side hose system 21 can be separated from the device-side connecting element 4 without a fluid communication being established between the lungs of the patient P and the surrounding area. The device-side hose system 21 to the ventilator 17 or to another ventilator can be connected again later to the device-side connecting element 4, and the patient P can be connected again to the ventilator 17 or to another ventilator.

In one embodiment, the two jaws 8.1 and 8.2 can be brought only into the releasing state or into a blocking state.

In another embodiment, the two jaws 8.1 and 8.2 can additionally be used to reduce the flow rate, i.e., the volume per unit of time, of a fluid flowing through the hose 7.1 without the fluid connection being completely interrupted. The two jaws 8.1 and 8.2 are compressed for this purpose to the extent that the distance between the two jaws 8.1 and 8.2 is between the maximum distance (no action on the hose 7.1) and the minimum distance (hose 7.1 fully compressed). The two jaws 8.1 and 8.2 then establish an intermediate state.

In the exemplary embodiment, the two jaws 8.1 and 8.2 are guided mechanically, while they are being transferred from one state into the other state relative to the connecting elements 3 and 4. Two holders 11.1 and 11.2 are connected permanently to the free end of a jaw 8.1 and 8.2, respectively. The holder 11.2 encloses the patient-side connecting element 3 both in the blocking state and in the releasing state. The patient-side connecting element 3 is passed through an elongated hole 13 in the holder 11.2. The holder 11.2 and hence the jaw 8.2 are therefore guided, while the jaw 8.2 is moved relative to the connecting elements 3 and 4. The holder 11.1 has the shape of a fork with two tines, wherein the two tines of the fork 11.1 enclose the patient-side connecting element 3 from two sides in the blocking state (FIG. 4) and each have a distance from the patient-side connecting element 3 in the releasing state (FIG. 2, FIG. 3). The two tines of the fork 11.1 guide the jaw 8.1, while the jaw 8.1 is being moved relative to the two connecting elements 3 and 4.

The two jaws 8.1 and 8.2 can be locked in the blocking state (FIG. 4) in the exemplary embodiment. A mechanical locking unit prevents the two jaws 8.1 and 8.2 from moving unintentionally away from one another and thereby the clamping unit from being moved unintentionally or from moving by itself into the releasing state or into an intermediate state. The locking unit comprises the two holders 11.1 and 11.2. A pair of hooks 12.1 at the two tines of the fork 11.1 meshes in the blocking state with two corresponding hooks 12.2 at the holder 11.2. As a result, the two jaws 8.1 and 8.2 are locked in the blocking state. In one embodiment of the exemplary embodiment (FIG. 4), three pairs of hooks 12.2 are arranged at the holder 11.2, so that the two jaws 8.1 and 8.2 can be locked relative to one another at one of three different possible distances relative to one another. More than 10 pairs of hooks are arranged in another embodiment (FIG. 2, FIG. 3). A different number of hook pairs at the holder 11.2 or also at the holder 11.1 are, of course, also possible. The embodiment with at least two hook pairs at a holder 11.2 and/or 11.1 makes it possible to lock the two jaws 8.1 and 8.2 in the blocking state or in a state in which a reduced flow rate through the hose 7.1 is still made possible, especially in an intermediate state.

A user can move the clamp 1 manually into the releasing state. To do so, the user releases the locking of the jaws 8.1, 8.2, for example, by moving the tines of the fork 11.1 away from the holder 11.2. The jaws 8.1 and 8.2 can then move away from one another by themselves or they can be moved away from one another, and they release the hose 7.1. It is possible that the two jaws 8.1 and 8.2 are mounted in a pretensioned state such that when they are not locked, they are in the releasing state or move into the releasing state by themselves.

Figure 5:
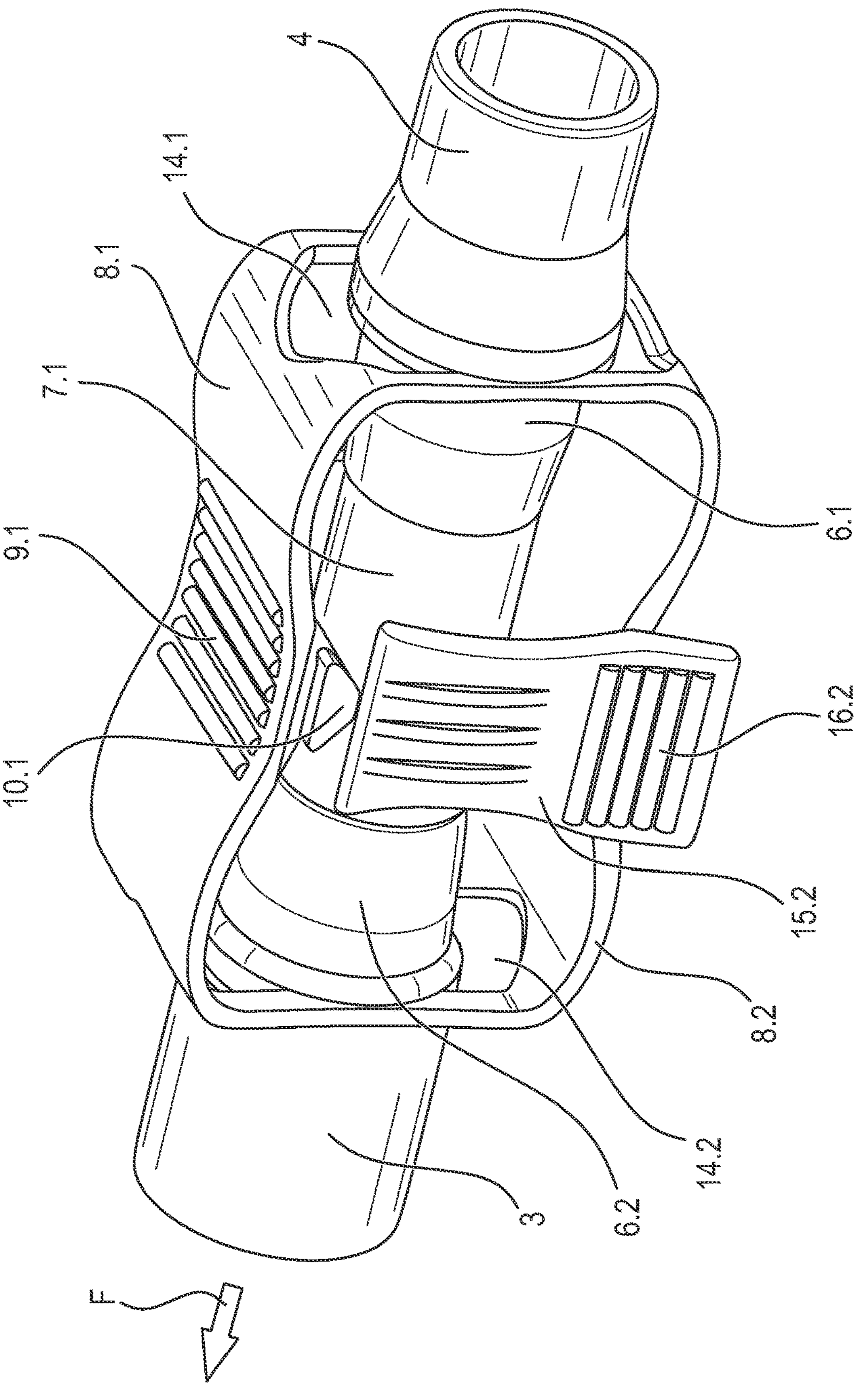
FIG. 5 is a perspective view showing a second embodiment of the clamp according to the present invention in the releasing state.
Figure 6:
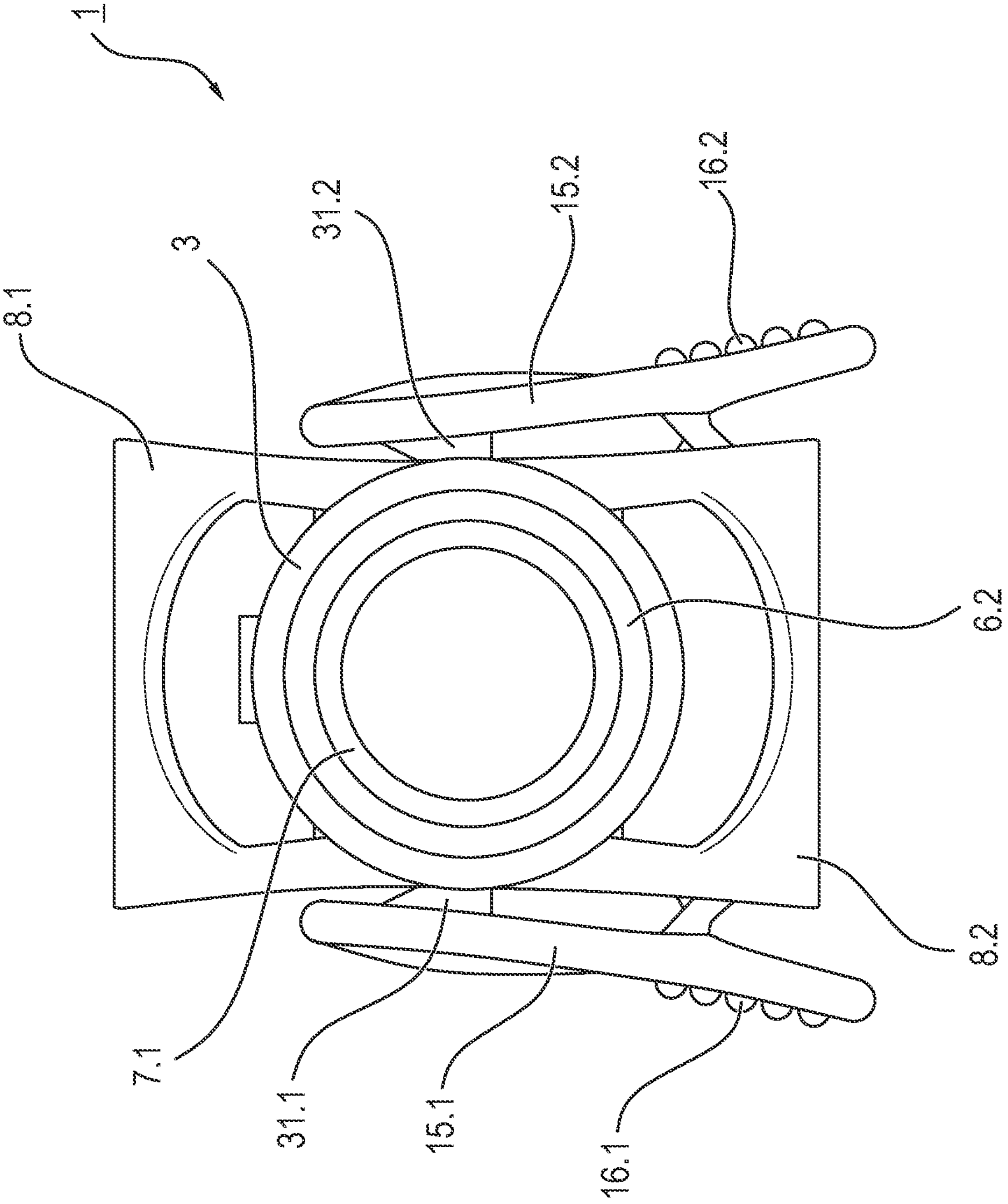
FIG. 6 is a front view showing the second embodiment according to FIG. 5 in the releasing state.
Figure 7:
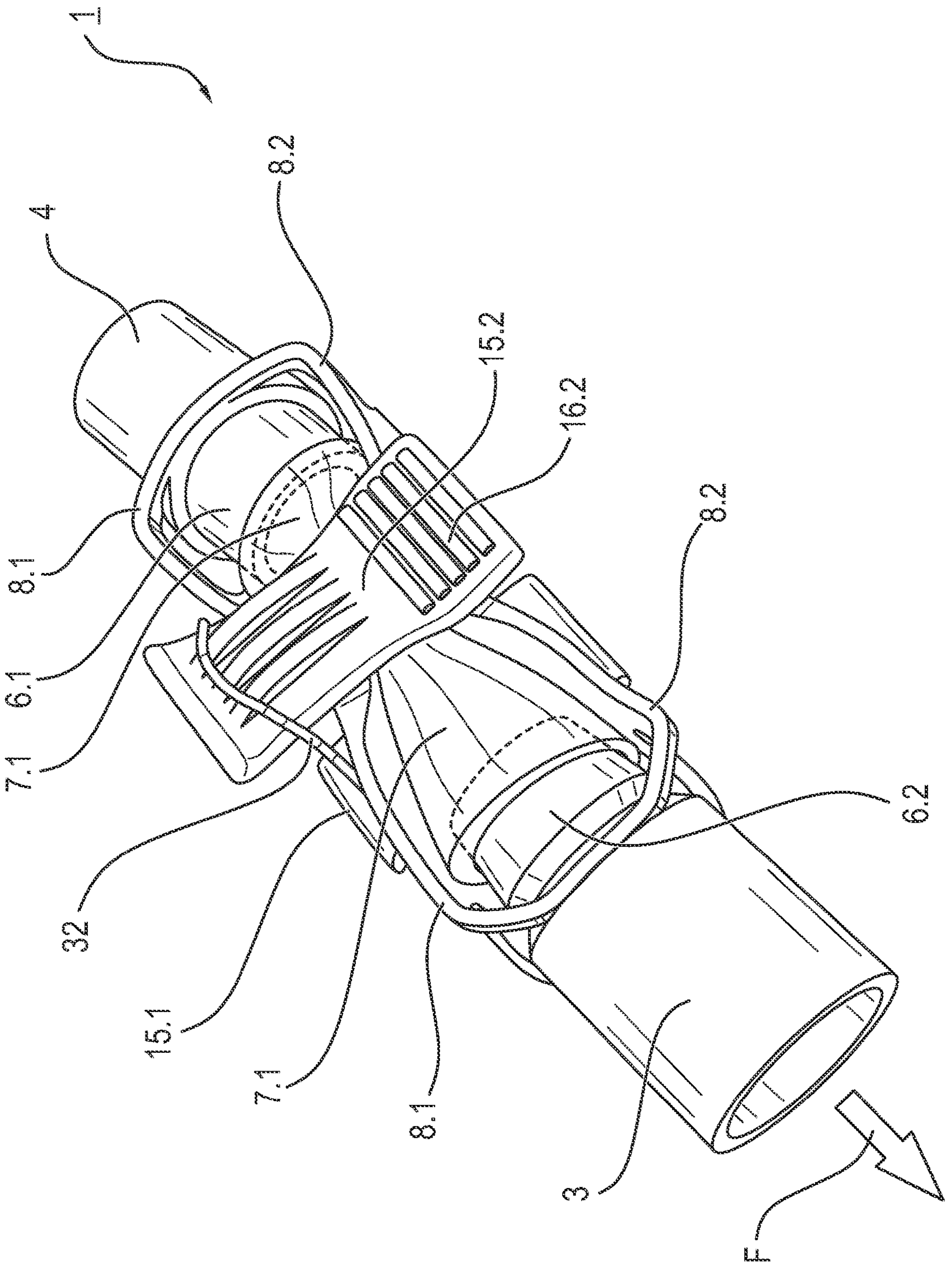
FIG. 7 is a perspective view showing the second embodiment according to FIG. 5 in the blocking state.

FIG. 5, FIG. 6, and FIG. 7 show a second embodiment of the clamp 1. Identical reference numbers have the same meanings as in the description of the first embodiment according to FIG. 2 through FIG. 4. The clamping unit 8.1, 8.2 is in the releasing state in FIG. 5 and FIG. 6 and in the blocking state in FIG. 7.

Contrary to the first embodiment, the two clamping components 8.1, 8.2 are connected to one another at both ends rather than at one end only in the second embodiment. A patient-side elongated hole 14.1, through which the patient-side connecting element 3 is passed, is formed between the patient-side ends of the two clamping components 8.1, 8.2. A device-side elongated hole 14.2, through which the device-side connecting element 4 is passed, is formed between the device-side ends. The two connecting elements 3 and 4 are permanently connected to the two ends of the two clamping components 8.1, 8.2. No webs 5.1, 5.2 are present in the second embodiment, especially because the connection between the two clamping components 8.1, 8.2 is mechanically more stable than in the first embodiment.

The two clamping components 8.1, 8.2 are flexible and can be compressed in a central area. Gripping elements 9.1, 9.2 are applied at least in this central area to the respective outer surface of the two clamping components 8.1, 8.2.

Two blocking snappers 15.1, 15.2 are connected to the lower clamping component 8.2 such that the lower clamping component 8.2 is located between these two blocking snappers 15.1, 15.2. The connection between the two blocking snappers 15.1, 15.2, on the one hand, and the lower clamping component 8.2, on the other hand, is established by two mechanical connection elements 30.1, 30.2. The two blocking snappers 15.1, 15.2 are rotatable relative to the lower clamping component 8.2 about two parallel axes of rotation, these axes of rotation extending through the two connection elements 30.1, 30.2 and being directed at right angles to the drawing plane of FIG. 6.

Two protruding locking bodies 31.1, 31.2 are placed on the two inner surfaces of the two blocking snappers 15.1, 15.2. These two locking bodies 31.1, 31.2 mesh with two gaps between the upper clamping element 10.1 and the upper clamping component 8.1 from two mutually opposite sides when the two clamping components 8.1, 8.2 are compressed and the clamping unit is therefore in the blocking state. The two elastically configured connection elements 30.1, 30.2 or a respective additional spring hold the two locking bodies 31.1, 31.2 in this meshing state.

Two gripping elements 16.1, 16.2 are placed on the two outer surfaces of the blocking snappers 15.1, 15.2. The two blocking snappers 15.1, 15.2 can be rotated relative to the lower clamping component 8.2 by a user compressing the two gripping elements 16.1, 16.2. As a result, the two locking bodies 31.1, 31.2 are pulled out of the two gaps. The two clamping components 8.1 and 8.2 move away from one another. As a result, the clamping unit is brought into the releasing state.

As can be seen in FIG. 7, an optional strap 32 is connected rotatably to the one blocking snapper 15.1. This strap 32 can be pushed over the other blocking snapper 15.2 and it will then prevent the two locking bodies 31.1 and 31.2 from moving away from one another. As long as the strap 32 is holding the blocking snapper 15.2, the strap 32 reduces the risk of the clamping unit being inadvertently brought into the releasing state. The clamp 1 according to the embodiment shown in FIG. 7 can also be embodied without such a strap 32.

Figure 9B:
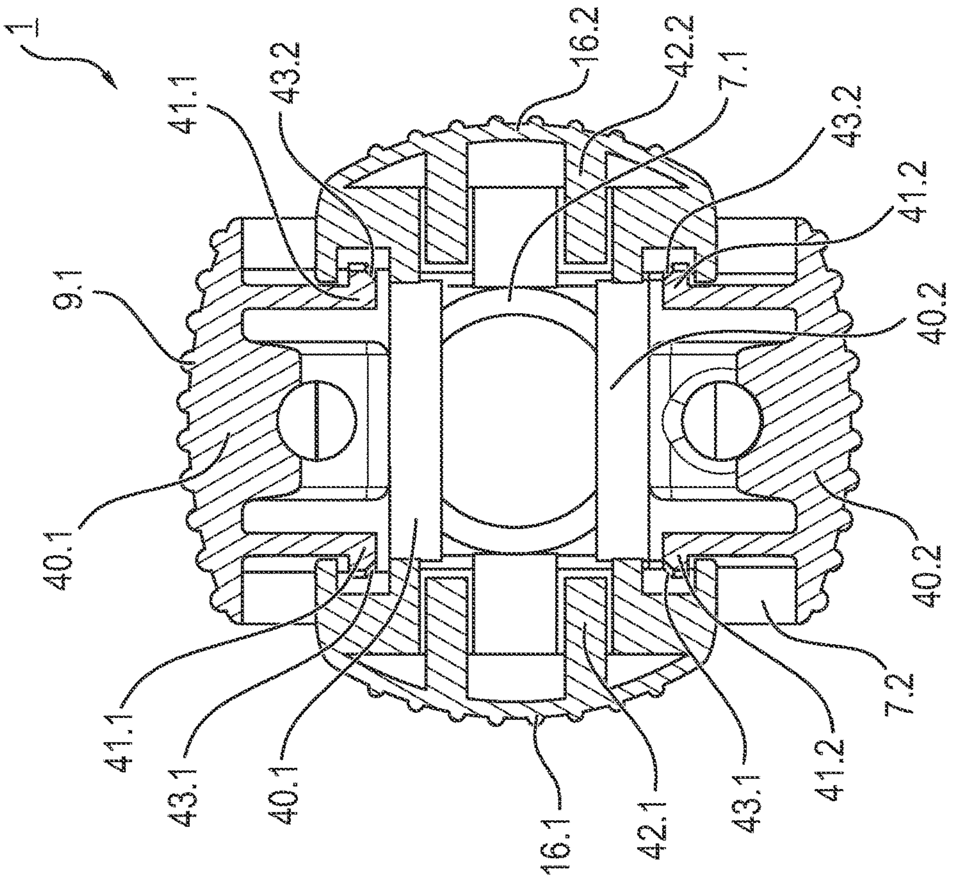
Figure 9A:
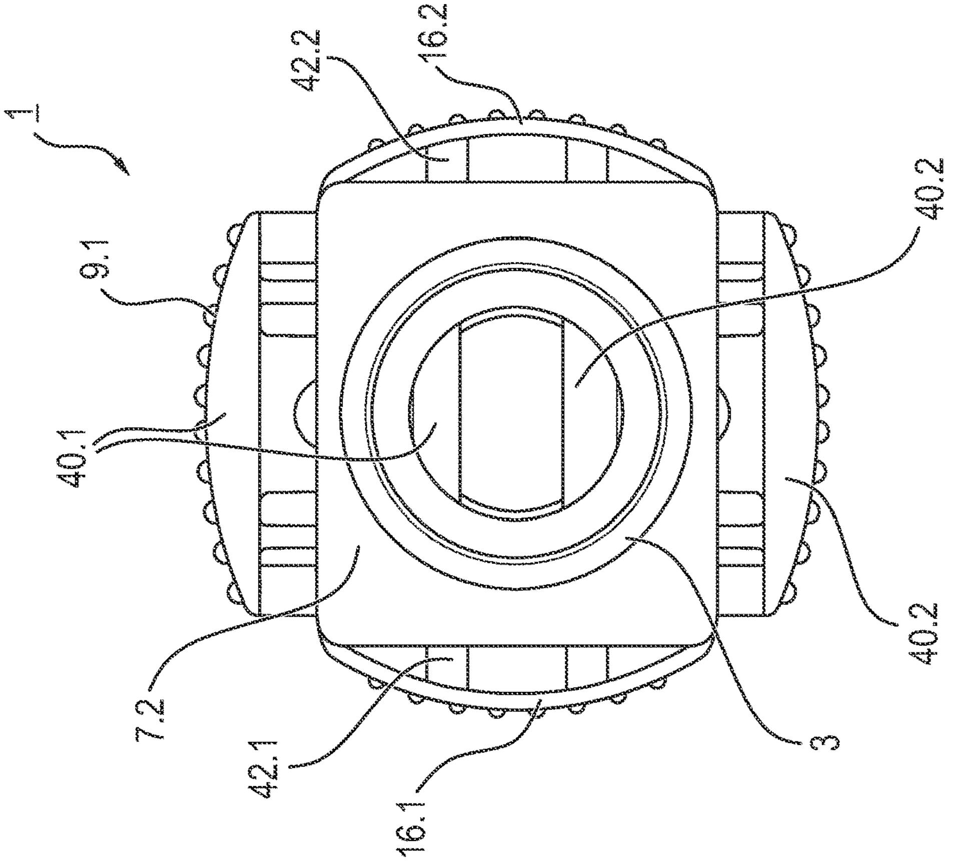

FIG. 8, FIG. 9, and FIG. 10 show a third embodiment of the present invention, where the clamping unit is in the releasing state in FIG. 8 and in FIG. 9 and in the blocking state in FIG. 10. FIG. 8 shows a perspective view of the clamp 1. FIG. 9*a*) shows a front view of the clamp 1, wherein the flow direction through the clamp 1 is at right angles to the drawing plane. FIG. 9*b*) and FIG. 10 show a sectional view in a centrally arranged plane, which is at right angles to the viewing direction of FIG. 9*a*).

It is possible to use a flexible hose 7.1 as the blocking fluid guide element in this third embodiment as well. The hose 7.1 is replaced, by contrast, by a rigid blocking fluid guide element 7.2 in the embodiment shown. This rigid blocking fluid guide element 7.2 is connected in a fluid-tight manner to the two connecting elements 3 and 4 and has the shape of a cuboid with rounded edges in this embodiment. Two circular openings, into which the connecting elements 3 and 4, respectively, are inserted, are recessed in two mutually opposite surfaces of this cuboid. A respective slot, which is at right angles to the flow direction of fluid through the clamp 1, is recessed in each of the four other surfaces. This flow direction is at right angles to the drawing planes of FIG. 9 and FIG. 10.

Two blocking sliders 40.1 and 40.2 with two gripping elements 9.1 and 9.2, respectively, located on the outside, are recessed in two slots located mutually opposite each other. These slots are arranged at the top and at the bottom, respectively, in the embodiment shown. The two blocking sliders 40.1 and 40.2 are movable linearly relative to the blocking fluid guide element 7.2, namely, in two mutually opposite directions, upwards and downwards in the view shown. In the blocking state, these two blocking sliders 40.1 and 40.2 touch each other at an edge and prevent a flow of fluid through the blocking fluid guide element 7.2. A distance occurs in the releasing state (FIG. 8, FIG. 9) between these two blocking sliders 40.1 and 40.2, so that a flow of fluid is made possible.

Two locking slides 42.1, 42.2 are recessed in the two other mutually opposite slots. The two locking slides 42.1, 42.2 are movable linearly relative to the blocking fluid guide element 7.2, namely, in two mutually opposite directions, to the left and to the right in the view shown. When the clamping unit is in the blocking state (FIG. 10), two pairs 41.1 and 41.2 of detents mesh at the blocking sliders 40.1 and 40.2 with corresponding recesses in the two locking slides 42.1 and 42.2. As a result, the two blocking sliders 40.1 and 40.2 are locked in the blocking state. The two locking slides 42.1 and 42.2 project over the blocking fluid guide element 7.2 over the maximum possible section.

To bring the blocking sliders 40.1 and 40.2 from the blocking state into the releasing state, the two locking slides 42.1, 42.2 are compressed, for example, by a user. Two pairs 43.1, 43.2 of bevels on the two locking slides 42.1, 42.2 press against the beveled detents 41.1, 41.2. As a result, the two blocking sliders 40.1, 40.2 are pushed apart and they release the blocking fluid guide element 7.2.

While specific embodiments of the invention have been shown and described in detail to illustrate the application of the principles of the invention, it will be understood that the invention may be embodied otherwise without departing from such principles.

LIST OF REFERENCE CHARACTERS

| | |
|---|---|
| 1 | Clamp; it comprises the connecting elements 3 and 4, the webs 5.1 and 5.2, the hose 7.1 or the rigid element 7.2 as well as the jaws 8.1 and 8.2 |
| 2 | Ventilation system; it comprises the ventilator 17 and the connection device 100; it is capable of delivering a gas mixture to the patient-side coupling unit 26 |
| 3 | Patient-side rigid connecting element of the clamp 1, connected to the patient-side hose system 18 |
| 4 | Device-side rigid connecting element of the clamp 1, connected detachably to the device-side hose system 21 |
| 5.1, 5.2 | Webs, which permanently connect the connecting elements 3 and 4 to one another in the first embodiment; they enclose the hose 7.1 from two sides |
| 6.1, 6.2 | Cones of the respective connecting elements 3 and 4 |
| 7.1 | Flexible blocking fluid guide element in the form of a hose, which connects the rigid connecting elements 3 and 4 to one another; it is pulled over the cones 6.1, 6.2; it can be compressed by the clamping components 8.1, 8.2 |
| 7.2 | Rigid blocking fluid guide element, which can be closed by the blocking sliders 40.1, 40.2 |
| 8.1, 8.2 | Clamping components, which together can clamp or release the hose 7.1 between them as desired; they are connected to the webs 5.1 and 5.2 in an articulated manner |
| 9.1, 9.2 | Gripping element in the form of a fluting, arranged on the outer surface of a clamping component 8.1 and 8.2 as well as 40.1, 40.2, respectively |
| 10.1, 10.2 | V-shaped clamping element, arranged on the inner surface of a clamping component 8.1, 8.2, respectively; it touches the hose 7.1 in the blocking state |
| 11.1 | Holder in the form of a fork; it encloses in the blocking state of the jaws 8.1, 8.2 the patient-side connecting element 3; it belongs to the locking unit of the first embodiment and acts as a guide element |
| 11.2 | Holder with the elongated hole 13; it encloses in both states of the jaws 8.1, 8.2 the patient-side connecting element 3; it belongs to the locking unit of the first embodiment |
| 12.1 | Pair of hooks at the holder 11.1; it belongs to the locking unit |
| 12.2 | Pairs of hooks at the holder 11.2; they belong to the locking unit |
| 13 | Elongated hole in the holder 11.2, through which the patient-side connecting element 3 is passed; it acts as a guide element |
| 14.1, 14.2 | Elongated holes in the clamping unit 8.1, 8.2, through which the two connecting elements 3, 4 are passed |
| 15.1, 15.2 | Blocking snappers of the second embodiment; they carry the locking bodies 31.1 and 31.2, respectively |
| 16.1, 16.2 | Gripping elements at the blocking snappers 15.1, 15.2 and at the locking slides 42.1, 42.2 |
| 17 | Ventilator, via which the device-side hose system 21 is connected to the clamp 1; it comprises the display and operating unit 19 |
| 18 | Patient-side hose system; it connects the patient-side coupling unit 26 to the patient-side connection 3 of the clamp 1; it belongs to the patient-side fluid guide unit |
| 19 | Display and operating unit at the ventilator 17 |

-continued

| | |
|---|---|
| 20 | Optional breathing air filter between the device-side hose system 21 and the ventilator 17 |
| 21 | Device-side hose system; it connects the ventilator 17 to the device-side connection 4 of the clamp 1 |
| 26 | Tube; it belongs to the patient-side coupling unit |
| 27 | Mouthpiece; it connects the patient-side hose system 18 or directly the clamp 1 to the tube 26; it belongs to the patient-side fluid guide unit |
| 29 | Filter for viruses, microbes, and bacteria, arranged in the device-side hose system 21 |
| 30.1, 30.2 | Connection elements, which connect the two blocking snappers 15.1, 15.2 to the lower clamping component 8.2 |
| 31.1, 31.2 | Locking bodies, arranged on the inside on the two blocking snappers 15.1, 15.2 |
| 32 | Optional strap, connected rotatably to the holder 15.1; it can be displaced over the holder 15.2 |
| 40.1, 40.2 | blocking slider which can close the rigid blocking fluid guide unit 7.2 |
| 41.1, 41.2 | Detents at the slides 40.1, 40.2 |
| 42.1, 42.2 | Locking slides for locking and unlocking the blocking sliders 40.1, 40.2 |
| 43.1, 43.2 | Bevels on the locking slides 42.1, 42.2; they can push the blocking sliders 40.1, 40.2 away from one another |
| 100 | Connection device; it comprises the patient-side coupling unit 26, the mouthpiece 27, the hose systems 21 and 18, the clamp 1 as well as the optional breathing air filter 20 and the optional filter 29 |
| DA | Axis of rotation, about which the two jaws 8.1 and 8.2 can be rotated relative to the device-side connecting element 4 and relative to one another |
| F | Flow direction, in which the gas mixture flows from the ventilator 17 to the patient-side coupling unit 26 |
| P | Patient, connected to the ventilator 17 via the patient-side coupling unit 26 and the connection device 100 |

What is claimed is:

1. A clamp for selectively releasing or blocking a fluid connection, the clamp comprising:

a clamping tube, the clamping tube comprising:

a blocking fluid guide element;

a first connecting fluid guide element; and a second connecting fluid guide element, wherein the blocking fluid guide element is fluid-tightly connected to the first connecting fluid guide element and is fluid-tightly connected to the second connecting fluid guide element;

a clamping unit comprising two clamping components; and a locking unit configured to lock the two clamping components and to thereby hold the clamping unit in a blocking state, wherein the blocking fluid guide element is located between the two clamping components, wherein the clamping unit is configured to selectively be brought into a releasing state or into the blocking state, wherein with the clamping unit being in the releasing state, the blocking fluid guide element establishes a fluid connection between the first connecting fluid guide element and the second connecting fluid guide element, and wherein with the clamping unit being in the blocking state, the two clamping components prevent a flow of fluid through the blocking fluid guide element or reduce a flow of fluid through the blocking fluid guide element by at least 80% compared to the releasing state and thereby interrupt or at least limit the fluid connection between the first connecting fluid guide element and the second connecting fluid guide element with the clamping unit in the blocking state.

2. A clamp in accordance with claim 1, wherein each connecting fluid guide element is or comprises a rigid tubular component; and wherein each clamping component is mechanically connected to a respective connecting fluid guide element, or the two clamping components are mechanically connected to the same connecting fluid guide element.

3. A clamp in accordance with claim 1, wherein the two connecting fluid guide elements are permanently mechanically connected to one another by at least one mechanical connection element.

4. A clamp in accordance with claim 1, wherein:

the blocking fluid guide element is flexible over its entire length or at least in one area; and with the clamping unit being in the blocking state, the two clamping components clamp the blocking fluid guide element in the flexible area between the two clamping components, whereby the flow of fluid through the blocking fluid guide element is reduced by at least 80% in the blocking state compared to the releasing state.

5. A clamp in accordance with claim 4, wherein:

the two clamping components each comprise a respective jaw;

the two jaws are articulated to each other in a V shape or U shape configuration or are connected linearly displaceable relative to each other; and the two jaws clamp the flexible blocking fluid guide element between the two jaws with the clamping unit being in the blocking state.

6. A clamp in accordance with claim 5, wherein:

the clamp comprises two guiding elements;

each jaw is associated with a respective one of the two guiding elements; and each of the two guiding elements is configured to guide the associated jaw during a movement of the jaw relative to the clamping tube.

7. A clamp in accordance with claim 6, wherein:

one of the two guiding elements has an elongated hole and the other of the two guiding elements comprises a fork;

the clamping tube is passed through the elongated hole in both the blocking state and the releasing state; and with the clamping unit being in the blocking state, the fork encloses the clamping tube from two sides.

8. A clamp in accordance with claim 1, wherein:

a distance between the two clamping components is variable;

the distance between the two clamping components with the clamping unit being in the blocking state is smaller than the distance between the two clamping components with the clamping unit being in the releasing state; and the locking unit is configured to lock the two clamping components being in a position of smallest distance to each other.

9. A connection device for establishing a fluid connection between a first device and a second device, the connection device comprising:

a first fluid guide unit being connectable with the first device;

a second fluid guide unit being connectable with the second device; and a clamp, the clamp comprising:

a clamping tube, the clamping tube comprising:

a blocking fluid guide element;

a first connecting fluid guide element; and a second connecting fluid guide element, wherein the blocking fluid guide element is fluid-tightly connected to the first connecting fluid guide element and is fluid-tightly connected to the second connecting fluid guide element;

a clamping unit comprising two clamping components; and a locking unit configured to lock the two clamping components and to thereby hold the clamping unit in a blocking state, wherein the blocking fluid guide element is located between the two clamping components, wherein the clamping unit is configured to selectively be brought into a releasing state or into the blocking state, wherein with the clamping unit being in the releasing state, the blocking fluid guide element establishes a fluid connection between the first connecting fluid guide element and the second connecting fluid guide element, wherein with the clamping unit being in the blocking state, the two clamping components prevent a flow of fluid through the blocking fluid guide element or reduce a flow of fluid through the blocking fluid guide element by at least 80% compared to the releasing state and thereby interrupt or at least limit the fluid connection between the first connecting fluid guide element and the second connecting fluid guide element, wherein the first connecting fluid guide element is fluid-tightly connected to the first fluid guide unit, and wherein the second connecting fluid guide element is fluid-tightly connected to the second fluid guide unit.

10. A connection device according to claim 9 as part of a ventilation system, the ventilation system further comprising:

a ventilator; and a patient-side coupling unit configured to be at least temporarily positioned in, or positioned on, or positioned at a body of a patient, wherein the first fluid guide unit is fluid-tightly connected to the patient-side coupling unit, wherein the second fluid guide unit is fluid-tightly connected to the ventilator, and wherein the ventilator is configured to cause a fluid to be conveyed through the connection device to the patient-side coupling unit.

11. A connection device according to claim 10, wherein:

the first connecting fluid guide element is permanently connected to the first fluid guide unit; and the second connecting fluid guide element is detachably connected to the second fluid guide unit.

12. A connection device according to claim 9, wherein:

the blocking fluid guide element is flexible over its entire length or at least in one area; and with the clamping unit being in the blocking state, the two clamping components clamp the blocking fluid guide element in the flexible area between the two clamping components, whereby the flow of fluid through the blocking fluid guide element is reduced by at least 80% in the blocking state compared to the releasing state.

13. A connection device according to claim 9, wherein:

the two clamping components each comprise a respective jaw;

the two jaws are articulated to each other in a V shape or U shape configuration or are connected linearly displaceable relative to each other; and the two jaws clamp the flexible blocking fluid guide element between the two jaws with the clamping unit being in the blocking state.

14. A process comprising:

providing a clamp for selectively releasing or blocking a fluid connection, the clamp comprising:

a clamping unit comprising two clamping components;

a locking unit configured to lock the two clamping components and to thereby hold the clamping unit in a blocking state; and a clamping tube, the clamping tube comprising:

a blocking fluid guide element;

a first connecting fluid guide element; and a second connecting fluid guide element;

locating the blocking fluid guide element between the two clamping components;

fluid-tightly connecting the blocking fluid guide element to the first connecting fluid guide element and to the second connecting fluid guide element;

selectively bringing the clamping unit into a releasing state or into the blocking state;

with the clamping unit being in the releasing state, the blocking fluid guide element establishing a fluid connection between the first connecting fluid guide element and the second connecting fluid guide element; and with the clamping unit being in the blocking state, the two clamping components preventing a flow of fluid through the blocking fluid guide element or reducing a flow of fluid through the blocking fluid guide element by at least 80% compared to the releasing state and thereby interrupting or at least limiting the fluid connection between the first connecting fluid guide element and the second connecting fluid guide element.

15. A process according to claim 14, wherein the clamp is provided as a component of a connection device, wherein the connection device establishes or is at least capable of establishing at least from time to time a fluid connection between a medical device and a patient-side coupling unit.

16. A process according to claim 14, wherein:

a computer program is provided on a non-transitory computer-readable medium;

the computer program is executable on a computer; and the computer program is configured to actuate a 3D printer during the execution, wherein the actuation of the 3D printer causes the 3D printer to produce the clamp.

17. A process according to claim 14, wherein:

a 3D printer is provided, which 3D printer comprises a processor and a memory;

a computer program is stored in the memory, which is a non-transitory computer-readable medium; and the processor is configured to execute the stored computer program and to actuate the 3D printer during the execution of the computer program such that the actuated 3D printer produces the clamp.

* * * * *